United States Patent
Ding et al.

(10) Patent No.: US 11,020,083 B2
(45) Date of Patent: Jun. 1, 2021

(54) FLEXIBLE APPLICATION OF CROSS-CALIBRATION FOR QUANTITATIVE FUNCTIONAL IMAGING

(71) Applicant: Siemens Medical Solutions USA, Inc., Malvern, PA (US)

(72) Inventors: Xinhong Ding, Buffalo Grove, IL (US); Manojeet Bhattacharya, Chicago, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 95 days.

(21) Appl. No.: 16/317,863

(22) PCT Filed: Sep. 19, 2016

(86) PCT No.: PCT/US2016/052457
§ 371 (c)(1),
(2) Date: Jan. 15, 2019

(87) PCT Pub. No.: WO2018/052447
PCT Pub. Date: Mar. 22, 2018

(65) Prior Publication Data
US 2019/0357872 A1    Nov. 28, 2019

(51) Int. Cl.
*A61B 6/00*    (2006.01)
*A61B 6/03*    (2006.01)
*G01T 1/164*   (2006.01)

(52) U.S. Cl.
CPC .............. *A61B 6/585* (2013.01); *A61B 6/037* (2013.01); *G01T 1/164* (2013.01)

(58) Field of Classification Search
CPC ....... A61B 6/037; A61B 6/585; A61B 6/4258; G01T 1/164; G01T 1/2985; G01T 1/1644;
(Continued)

(56) References Cited

U.S. PATENT DOCUMENTS

| | | | | | |
|---|---|---|---|---|---|
| 5,311,427 | A | * | 5/1994 | Ichihara | ................ G01T 1/1648 250/363.04 |
| 5,491,342 | A | * | 2/1996 | Lim | ...................... G01T 1/1648 250/252.1 |

(Continued)

OTHER PUBLICATIONS

"Quality Assurance for SPECT Systems," IAEA Human Health Series, No. 6, International Atomic Energy Agency, Vienna, pp. 1-263, 2009.

(Continued)

*Primary Examiner* — Dani Fox
*Assistant Examiner* — Soorena Kefayati

(57) ABSTRACT

During calibration of a SPECT system, system-specific sensitivities and cross-calibration factors for multiple isotopes for correcting for dose are determined for various combinations of options, including the option of which specific well counter with which to measure the dose. The options may include selected energy windows for isotopes with multiple energy windows. This arrangement allows for custom-specified isotopes not included in standard listings. For use with a particular patient, the cross-calibration factor for the well counter used to measure the dosage for the patient is accessed and used for dose correction. More accurate quantitative functional information may result from the corrected dose. The cross-calibration may be more easily implemented despite the options using the sensitivities and cross-calibrations provided for various combinations.

20 Claims, 10 Drawing Sheets

(58) Field of Classification Search
CPC ... G01T 1/1645; G01T 1/1647; G01T 1/2026; G01T 1/1648; G01T 7/005
See application file for complete search history.

(56) References Cited

U.S. PATENT DOCUMENTS

| | | | | |
|---|---|---|---|---|
| 7,272,207 | B1* | 9/2007 | Aufrichtig | A61B 6/032 378/116 |
| 9,364,192 | B2* | 6/2016 | Vija | A61B 6/5258 |
| 2002/0165686 | A1* | 11/2002 | Kropfeld | G01T 1/2985 702/104 |
| 2005/0145797 | A1* | 7/2005 | Oaknin | G06T 11/006 250/363.04 |
| 2005/0201513 | A1* | 9/2005 | Nukui | G01T 1/2985 378/19 |
| 2008/0251708 | A1* | 10/2008 | Cresens | G01T 1/2012 250/252.1 |
| 2009/0127449 | A1* | 5/2009 | Iwatschenko-Borho | G01T 1/40 250/252.1 |
| 2009/0194677 | A1* | 8/2009 | Allberg | G01T 1/2002 250/252.1 |
| 2010/0174180 | A1* | 7/2010 | Rousso | A61B 6/037 600/431 |
| 2012/0053847 | A1* | 3/2012 | DeVito | G01T 1/167 702/22 |
| 2013/0124103 | A1* | 5/2013 | Mabie | G01T 1/167 702/23 |
| 2013/0131422 | A1* | 5/2013 | Vosniak | A61B 6/037 600/1 |
| 2013/0248719 | A1* | 9/2013 | Volokh | A61B 6/03 250/362 |
| 2014/0014828 | A1* | 1/2014 | Bredno | G06T 11/005 250/252.1 |
| 2014/0257566 | A1* | 9/2014 | Engell | G16H 40/40 700/268 |
| 2014/0371580 | A1* | 12/2014 | Bhattacharya | A61B 6/582 600/426 |
| 2015/0147273 | A1* | 5/2015 | Lappchen | A61K 49/0008 424/1.89 |
| 2015/0196268 | A1* | 7/2015 | Bhattacharya | A61B 6/037 600/425 |
| 2016/0223694 | A1* | 8/2016 | Griesmer | G01T 1/1647 |
| 2017/0090050 | A1* | 3/2017 | Chuang | G01T 7/005 |
| 2017/0172527 | A1* | 6/2017 | Uber, III | A61B 6/5264 |
| 2018/0021005 | A1* | 1/2018 | Conner | A61B 6/5205 600/431 |

OTHER PUBLICATIONS

Anne Larsson., "Corrections for improved quantitative accuracy in SPECT and planar scintigraphic imaging," Department of Radiation Sciences, Radiation Physics, Umea University, Sweden, pp. 1-88, 2005.
International Search Report for Corresponding Application No. PCT/US2016/052457, dated Dec. 8, 2016.
Zanzonico, P.; "Routine Quality Control of Clinical Nuclear Medicine Instrumentation: A Brief Review"; J Nucl Med. Jul. 2008 49(7). Retrieved Nov. 4, 2016 from <https://www.ncbi.nlm.nih.gov/pmc/articles/PMC2703015/pdf/nihms108996.pdf>.
Roy, et al.; "Residual syringe activity: Is there a need for concern?"; J Nucl Med May 2010 vol. 51.
Lilli Geworski et al: "Multicenter comparison of calibration and cross calibration of PET Scanners ", Journal of nuclear medicine: official publication, Society of Nuclear Medicine, May 1, 2002, pp. 635-639.
Extended European Search Report for Corresponding EP Application No. 16916375.7, dated Jul. 6, 2020.

* cited by examiner

```
                                            78
┌─────────────────────────────────────────────────────┐
│ 🗎 CAMERAPRESET.TXT-NOTEPAD              _ □ X      │
├─────────────────────────────────────────────────────┤
│ FILE  EDIT  FORMER  VIEW  HELP                      │
├─────────────────────────────────────────────────────┤
│                                                     │
│ @================                                   │
│ ISOTOPE:_IN_111_                                    │
│ ---- ADD PRESET BELOW----   80                      │
│ IN_111_                                             │
│ IN-111-                                             │
│                                                     │
│ @================                                   │
│ ISOTOPE:_IO_123_                                    │
│ ----ADD PRESET BELOW----    80                      │
│ IO_123                                              │
│ IO-123                                              │
│                                                     │
│ @================                                   │
│ ISOTOPE:_LU_177_                                    │
│ ----ADD PRESET BELOW----    80                      │
│ LU_177                                              │
│ LU-177                                              │
│                                                     │
│ @================                                   │
│ ISOTOPE:_SE_75_                                     │
│ ----ADD PRESET BELOW----    80                      │
│ SE_75                                               │
│ SE-75                                               │
│ TEST-SE-12                                          │
│                                                     │
│ @================                                   │
│ ISOTOPE:_YT_90_                                     │
│ ----ADD PRESET BELOW----    80                      │
│ YT_90                                               │
│ YT-90                                               │
│                                                     │
│ @================                                   │
│ ~END                                                │
│                                                     │
└─────────────────────────────────────────────────────┘
```

FIG. 11

FLEXIBLE APPLICATION OF CROSS-CALIBRATION FOR QUANTITATIVE FUNCTIONAL IMAGING

BACKGROUND

The present embodiments relate to calibration for functional imaging. Calibration is provided for quantitative functional imaging.

Functional imaging uses a radioisotope or radiotracer to determine metabolic function within a patient. For example, the uptake of the radiotracer by tissues in the body is measured. Positron emission tomography (PET) and single photon emission computed tomography (SPECT) are two types of functional imaging. The emissions from the radiotracer are detected in the functional imaging. The activity concentration (i.e., the concentration of the radiotracer from different locations) is reconstructed from the detected emissions.

The reconstruction uses the sensitivity of the detector for the quantitative reconstruction of emissions. This sensitivity may be calibrated, but contributes a possible source of error in quantitative functional imaging. If a class standard sensitivity is used, the detector specific sensitivity may be different. Similarly, the uncertainty of the exact dose applied to the patient introduces another source of error in quantitative functional imaging. The dose value for the liquid isotope applied to the patient may be inaccurate.

For quantitative functional imaging, both accurate activity concentration and uptake values are desired. The goal is to provide a global baseline that is free of system (detector and dose calibrator) variability so that any measured change for a patient over time in either quantity is due to metabolic reasons. U.S. Published Patent Application No. 2015/0196268 teaches cross-calibration to remove or reduce injected dose error and detector sensitivity error in quantitative functional imaging. By using measures from both the radiotracer for the patient and factory calibrated sources, the variability due to dose may be removed. However, cross-calibration may be difficult to implement given the various options available for functional imaging.

BRIEF SUMMARY

By way of introduction, the preferred embodiments described below include methods, systems, and non-transitory computer readable media for application of cross-calibration for a quantitative SPECT or other functional imaging system. During calibration of a SPECT system, system-specific sensitivities and cross-calibration factors for multiple isotopes for correcting for dose are determined for various combinations of options, including the option of which specific well counter with which to measure the dose. The options may include selected energy windows for isotopes with multiple energy windows. This arrangement allows for custom-specified isotopes not included in standard listings. For use with a particular patient, the cross-calibration factor for the well counter used to measure the dosage for the patient is accessed and used for dose correction. More accurate quantitative functional information may result from the corrected dose. The cross-calibration may be more easily implemented despite the options using the sensitivities and cross-calibrations provided for various combinations.

In a first aspect, a method is provided for application of cross-calibration for a quantitative SPECT system. The SPECT system at a facility has a detector configured to operate with different collimators to detect emissions from liquid radiotracers with injected dosages measured by well counters. The liquid radiotracers include isotopes. A first table of system specific planar sensitivities is generated. The first table includes one of the system specific planar sensitivities for each unique combination of isotope, energy of isotope, collimator, detector, and well counter. A second table of cross-calibration factors is generated. The second table includes one of the cross-calibration factors for each unique combination of the isotope, the collimator, the energy of the isotope, the detector, and the well counter. The cross-calibration factors are a function of the system specific planar sensitivities. Identities of a first one of the well counters used for a patient, a first one of the collimators used for the patient, a first one of the detectors used for the patient, a first one of the doses used for the patient, and a first one of the isotopes used for the patient are received. A dose correction is calculated with a first one of the cross-calibration factors selected based on the identities. Activity concentration in a patient having the first isotope at the first dose measured by the first well counter and corrected with the dose correction is estimated. The activity concentration is estimated from a scan by the SPECT system using the first detector and first collimator. An image of the activity concentration is generated.

In a second aspect, a non-transitory computer readable storage medium has stored therein data representing instructions executable by a programmed processor for application of cross-calibration in a SPECT system. The storage medium includes instructions for: receiving input of identity of first and second radioactive sources, searching for characteristics of the first and second radioactive sources from a standardized list of sources and from a custom list of un-standardized sources, determining system-specific sensitivity for the SPECT system and a cross-calibration factor relating radioactive sources, the determining being a based on the characteristics, and generating a quantitative SPECT image as a function of the system-specific sensitivity and the cross-calibration factor.

In a third aspect, a system is provided for application of cross-calibration in functional imaging quantification. A processor is configured to determine a sensitivity for a detector of a functional imaging system. The sensitivity is responsive to a measure by a well counter. The processor is configured to determine a cross-calibration between first and second isotope sources as a function of the sensitivity. The cross-calibration is specific to the well counter.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIG. 5 illustrates an example user interface for inputting dose and well counter information;

FIG. 6 is an example list with added isotopes for customization beyond standard isotopes;

FIG. 11 illustrates an example user interface for inputting well counter and energy windows and outputting cross-calibration information.

DETAILED DESCRIPTION OF THE DRAWINGS AND PRESENTLY PREFERRED EMBODIMENTS

Figure 1:
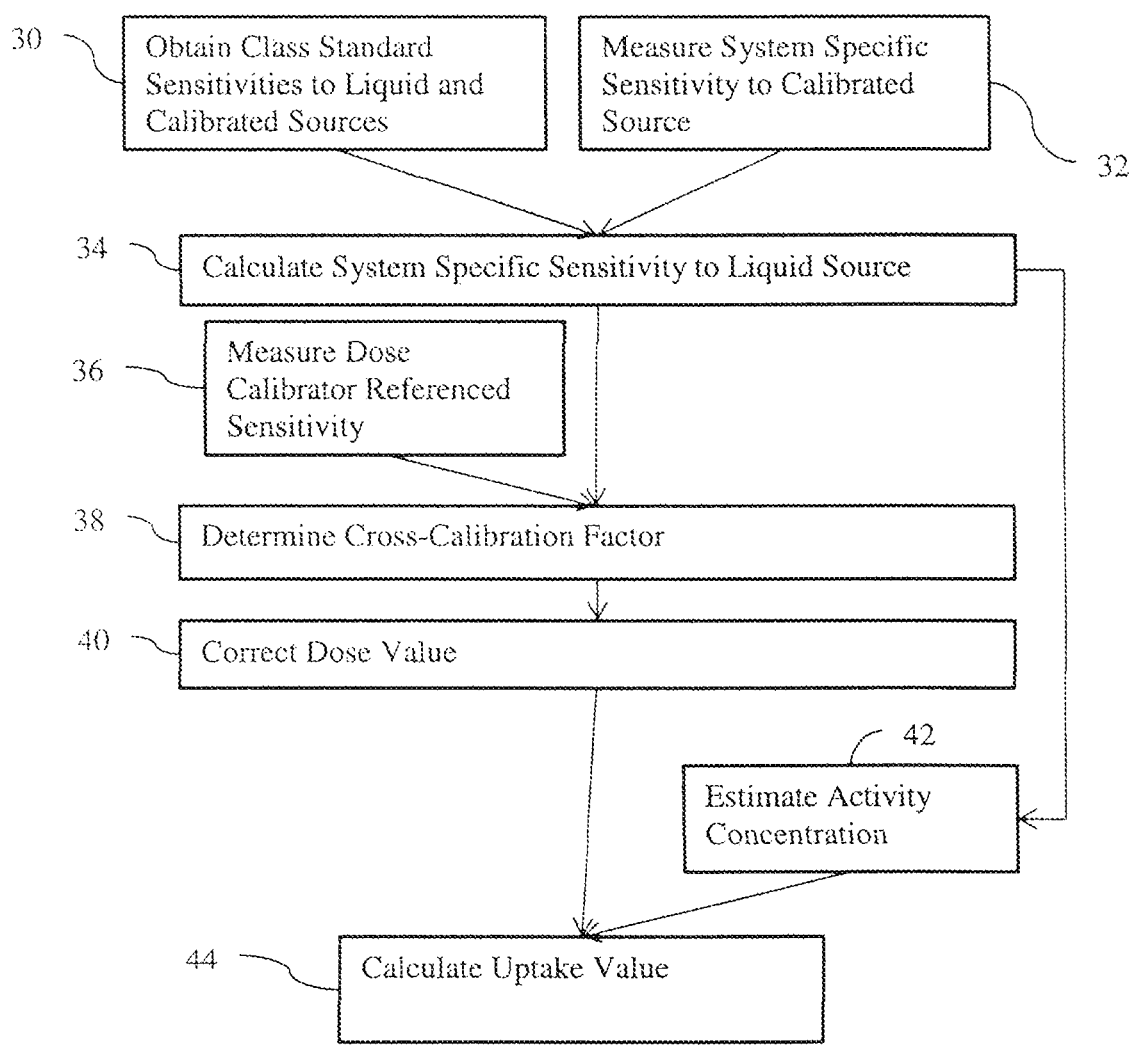
FIG. 1 is a flow chart diagram of one embodiment of a method for cross-calibration in functional imaging.

A general framework for cross-calibration is provided for quantitative SPECT imaging. In U.S. Published Patent Application No. 2015/0196268, cross-calibration is taught for quantitative SPECT imaging. Cross-calibration captures the calibration uncertainty of the well counter(s) in a clinical site using two radioactive sources, with one of the radioactive sources being a factory calibrated with National Institute of Standards and Technology (NIST) traceability. In any quantitative assessments of functional medical imaging in general, and SPECT imaging in particular, one of the key quantities is the dose injected into an object (e.g., patient or phantom) under study. This quantity typically is based on a reading of a well counter (dose calibrator). Different clinical sites may use different well counters and may have different calibration standards. As a result, there will be variations in terms of the accuracy of the measurements. To overcome this variability within a clinical site and among different sites, the system specific sensitivities in each clinical site are cross-calibrated with a set of pre-calculated class standard sensitivities.

A framework to carry out this cross calibration is provided. The framework includes three modules: a module to estimate the detector sensitivities for a given isotope, with proper energy ranges of the isotope, and the collimators used; a module to compute the system specific cross-calibration factors based on two isotopes; and a module to apply the cross-calibration factors to correct the injected dose during clinical applications. This framework is general (e.g., the framework can handle any radio isotopes available for medical imaging and/or can handle combinations of photo-peak energy ranges and scattered photon energy ranges), is flexible (e.g., options for the user interface and configurable settings), and is easy to use (e.g., deployed on a SPECT system). The framework accounts for different well counters, so the cross-calibration is specific to the well counter. The remaining specification is divided into two portions. The first portion (Cross-Calibration) discloses cross-calibration as provided in U.S. Published Patent Application No. 2015/0196268. The second portion (Application of or Framework for Cross-Calibration) then adds the framework or application of the cross-calibration. This application includes incorporation of considerations for non-standard isotopes, isotopes with multiple energy windows, and well-counter specific considerations for the cross-calibration.

Cross-Calibration

Rather than including inaccuracy from liquid radioisotope measures, a system specific sensitivity of the detector to a factory calibrated long-lived point source is measured and used to calculate sensitivity of the detector to the liquid radioisotope. A ratio of class standard sensitivities for long lived and liquid radioisotopes is used with the measured system specific sensitivity to a factory calibrated long-lived point source to calculate the system specific sensitivity to the liquid radioisotope. A cross-calibration factor for correcting the injected dose of liquid radioisotope is a ratio of the calculated system specific sensitivity to the liquid radioisotope and a measured liquid radioisotope sensitivity referenced to the dose calibrator. The calculated system specific sensitivity to the liquid radioisotope is used in reconstruction of the activity concentration, providing accurate activity concentration despite variability in the dose. The corrected dose and activity concentration are used to quantify accurate uptake despite the use of class standards.

This approach provides global as well as local baselines by eliminating both camera and dose calibrator variability. Different quantitative measures for a patient at different times and/or with different functional imaging systems are comparable. The quantitative evaluation is comparable across populations or between patients, assisting in diagnosis and/or therapy for a given patient. Any changes over time are more likely due to change in function rather than detector or dose variance.

FIG. 1 shows one embodiment of a method for cross-calibration in quantitative single photon emission computed tomography (SPECT) or positron emission tomography (PET). Other functional imaging may be used. For activity concentration estimation or uptake calculation (e.g., specific uptake value calculation), the dose and detector sensitivity are calibrated in a way removing variability due to both dose and detector. The examples below are provided for SPECT, but may be used in PET or other functional imaging modality.

The method is applied for a given scan of a given patient. By applying the method to different scans of the patient, the resulting quantities may be compared and have little to no variance due to differences in dose and detector. The different scans use the same or different detectors and/or doses. Similarly, the quantities may be compared between patients to establish norms or deviation from norm. Without the cross-calibration, comparison of activity concentration or uptake over time, detectors, doses, and/or patients is subject to variance unrelated to the metabolic function of the patient or patients.

Additional, different, or fewer acts may be performed. For example, acts 36-40 are not provided. As another example, acts 42 and/or 44 are not provided. In other examples, acts related to positioning the patient, configuring the SPECT scanner, and/or SPECT imaging are provided.

The acts are performed in the order shown or a different order. For example, act 36 is performed prior to act 34. As another example, act 42 is performed before act 40, 38, and/or 36. Acts 30 and 32 may be performed in any order.

In act 30, class standard sensitivities of the detector are obtained. The sensitivities are obtained by loading from memory, transfer, and/or measurements. Averages of multiple independent measurements from a number of different systems in the same class may be used.

For SPECT, the sensitivities are planar sensitivities of a gamma camera class. The detectors include photomultiplier tubes or other photon detectors layered with a scintillation crystal. The photomultiplier tubes are arranged along a rectangular or other grid to provide a two-dimensional planar array for detecting gamma radiation. Other types of detectors may be used, such as a ring of detectors in PET.

Any class or grouping may be used, such as defining a class as a given construction (e.g., materials and array configuration) with or without a specific collimator and/or scintillator crystals. For a given class, a number of different gamma cameras are manufactured to be used in a respective number of different SPECT systems. Different types of SPECT systems may use the same or different class of detectors.

The class of detectors has a class sensitivity to radiation sources. Different classes have different sensitivities. Within a class, given detectors may have different sensitivities, but generally have similar sensitivities. For a class sensitivity, the average sensitivity is calculated from measurements by any number (e.g., tens or hundreds) of members of the class.

To determine the class standard sensitivity, a point or other source of gamma radiation is positioned at a fixed distance (e.g., 20 cm) from the detectors. Counts of detected gamma photons from both the main photo peak(s) and the scatter(s) are collected by the detectors. The time from the first count to a given number of counts is determined. The sensitivity is the number of main photo peak(s) counts, after scatter correction, divided by the time and the dose of the source. Other calculations of sensitivity may be used.

Class standard (CS) sensitivity, $S_{LL}(CS)$, is measured for a factory calibrated long-lived (LL) point source. Any size point source may be used, such as 1 mm³. The long-lived or factory calibrated point source has a known dosage that is precise. Any amount of precision or tolerance may be provided, such as being more precise (e.g., by a factor of 10) than of a dose of a lab provided liquid radiotracer.

Class standard sensitivity, $S_{LR}(CS)$, is also measured for a liquid radiotracer (LR). The liquid radiotracer is encased in a sphere or other phantom to act as a point source. The detector sensitivity to the liquid radiotracer is measured by the various detectors and averaged. For determining a class standard, different batches of the radiotracer may be provided at different times to measure with all members of the group of detectors of the testing class. Alternatively, one batch is used for all of the class standard sensitivity measurements. Since the dose of the liquid radiotracer has more variability or is less precise, the resulting class standard sensitivity for the liquid radiotracer may be less precise than the class standard sensitivity for the long-lasting point source.

Any radiotracer may be used, such as 99Tc. The class standard sensitivity for the long-lived point source has a dose that is close (e.g., within 10%) or the same as for the liquid radiotracer. The class standard sensitivities for the liquid radiotracer are for the same radiotracer to be used for patient examination. For example, different class standard sensitivities are obtained for different radiotracers. Alternatively, the class standard for the liquid radiotracer is a different radiotracer than used for examining a patient.

In act 32, a system specific sensitivity, $S_{LL}(SS)$, of a detector to a long-lived point source is measured using the detector, a timer, and processor. For a given SPECT system, the planar gamma camera is used to measure sensitivity. The sensitivity of the specific SPECT system gamma camera of the class of cameras is measured.

The same or different long-lived point source used for determining the class standard is used. For example, a technician periodically maintains or calibrates a given SPECT system at a medical institution. As part of the maintenance, the system specific sensitivity to a long-lived point source provided and positioned by the technician is measured. This is a different point source than used for the class standard measurements used by others at a testing lab, manufacturing facility, or other medical institutions. In another example, the system specific sensitivity to the long-lived or factory calibrated point source is measured after manufacture but before providing to the medical institution. The same point source used for the class is used. Alternatively, a different point source with the same or similar (e.g., within 10%) dose in Becquerel is used. Due to the factory calibration of the long-lived point source, the same calibration accuracy, independent of the site dose calibrator, is provided. In yet other embodiments, the point source used has a difference in energy greater than 10% from the point source used in the class standard measurements. Using a known dose provided with the precision of factory calibration, the sensitivity of the gamma camera is measured with less variability as compared to measurements from liquid radiotracers.

The same or different sensitivity measure is used for the system specific sensitivity as for the class standard. For example, the time to reach a given number of counts with the dose known for the point source is used. The number of counts used in both the class standard and system specific measurements is the same or different.

In act 34, a system specific sensitivity, $S_{LR}(SS)$, to a liquid radiotracer is calculated. Rather than measuring the system specific sensitivity using the liquid radiotracer to be injected into a patient, a processor calculates the system specific sensitivity. For SPECT, the system specific sensitivity is a planar sensitivity of a gamma camera. Placing the radiotracer in a phantom or point source container may be avoided. Instead, the sensitivity of the specific detector is calculated using various other information, such as the class standard sensitivity to a radiotracer with the same or similar energy or dose in Becquerel.

The system specific sensitivity to the liquid radiotracer is calculated using the class standard sensitivities of the detector class (e.g., type of planar gamma camera class) to the liquid radiotracer source and the long-lived source of act 30. The system specific sensitivity of the detector (e.g., gamma camera) to the long-lived source measured in act 32 is also used in calculating the system specific sensitivity to the liquid tracer. In one embodiment, the system specific sensitivity is calculated as a result of a (1) product of the class standard planar sensitivity to the liquid radiotracer source with the system specific planar sensitivity to the long-lived source being (2) divided by the class standard planar sensitivity to the long-lived source. This function is represented as:

$$S_{LR}(SS)=(S_{LR}(CS) \times S_{LL}(SS))/S_{LL}(CS).$$

The ratio of the class standard sensitivities for liquid and long-lived sources is assumed to be the same as the ratio of system specific sensitivities for liquid and long-lived sources. Since the precise system sensitivity to the long-lived source is measured in act 32, the liquid radiotracer sensitivity is derived by the processor. Reliance of the dose calibration accuracy for the liquid radiotracer is avoided. Other functions with or without constants or different mathematical operations may be used. In an alternative embodiment, the system specific sensitivities for both the reference source and the injected source is an independent calculation that does not use information from class standard sensitivity.

In act 36, a dose calibrator referenced liquid radiotracer sensitivity, $S_{LR}(XC)$, is measured and received. The processor receives the dose value from user input, loading from memory, or network transfer. In one embodiment, the dose calibrator referenced sensitivity is measured using a local dose calibrator and the gamma camera. For example, the dose calibrator referenced liquid radiotracer sensitivity is measured as disclosed in U.S. Published Application No. 2014-0371580. A detector of a gamma camera is configured such that a radioactive point source is positioned within a field of view at a fixed distance from the detector. A predetermined number of gamma photons emitted by the point source and passed through a collimator are acquired. A system-specific planar sensitivity is computed for a combination of the collimator and detector using the number of gamma photons acquired, a time duration of the acquisition, and precalibrated radioactivity data of the point source corrected for decay that occurred after a precalibration time. For example, the measure performed in act 32 is used.

A deviation of the computed system-specific planar sensitivity from a class standard sensitivity value for a combination of the radioactive point source, the collimator, and the detector is computed. A class standard sensitivity value for a combination of a radiopharmaceutical, the collimator, and the detector is scaled by the computed deviation, yielding a scaled system-specific sensitivity value for the radiopharmaceutical. Other approaches may be used, such as measuring a ratio of observed counts to number of disintegrations in the radioactive source of a dose calibrator. This measurement is received by the acquisition computer.

The lab providing the liquid radiotracer to inject into the patient provides dose, such as a value in Becquerel. This dose is of the same type of liquid radiotracer used for the class standard sensitivity measurements, but may be of a different type of radiotracer. The lab provides the dose value of the liquid radiotracer measured using the local dose calibrator.

In act 38, a cross-calibration factor, $F_{XC}$, is determined. The cross-calibration factor accounts for both the detector sensitivity and the dose or liquid radiotracer sensitivity. The dose calibrator referenced liquid radiotracer sensitivity, $S_{LR}(XC)$, of the liquid radiotracer to be injected into the patient and the system specific planar sensitivity to the liquid radiotracer are combined as a cross-calibration function. Both the calibration for the dose and the calibration for the system specific detector are used. Other terms may be used.

In one embodiment, the cross-calibration factor is a ratio. The system specific planar sensitivity to the liquid radiotracer is divided by the dose calibrator referenced liquid radiotracer sensitivity, as represented by:

$$F_{XC}=S_{LR}(SS)/S_{LR}(XC)$$

This function provides a ratio of measured to derived sensitivity. The cross-calibration value is a function of a system specific sensitivity to a patient specific radiotracer calculated from the system specific sensitivity to the long-lived point source and a dose calibrator referenced radiotracer sensitivity. Other functions may be used.

In act 40, a dose value is corrected by the processor. The dose value is of the liquid radiotracer to be injected into the patient. The lab providing the radiotracer provides the dose, such as a value in Becquerel. The dose value is used in calculating uptake from the activity concentration. Prior to such use, the dose value is corrected using the cross calibration factor.

The dose value is corrected with the cross-calibration factor. Since the cross-calibration factor includes the system specific sensitivity to the long-lived point source through the calculation of the system specific sensitivity to the liquid radiotracer, the correction is a function of the system specific sensitivity of the factory calibrated, long-lived point source. Correcting the injected dose by $F_{XC}$ may result in accurate uptake values free of either camera specific or local dose calibrator specific variations. Variations due to potentially asynchronous clocks between the camera system and the dose calibrator may be removed by the correction.

For correction, the cross-calibration factor is used directly. For example, the dose value is multiplied by or with the cross-calibration value. Other functions may be used. In alternative embodiments, the cross-calibration factor is used to look-up a weight or other adjustment applied to the dose value. In either the direct or indirect sense, the injected dose value for a radiotracer used in a patient is corrected with the cross-calibration value.

In act 42, the activity concentration is estimated. The activity concentration in a patient having received the liquid radiotracer is determined as part of reconstruction by the functional imaging system. After ingesting or injecting the radiotracer into the patient, the patient is positioned relative to the detector and/or the detector is positioned relative to the patient. Emissions from the radiotracer within the patient are detected over time. To determine the locations within the patient at which the emissions occurred, the detected emissions are reconstructed into an object space.

For reconstruction, the activity concentration (e.g., quantitative SPECT) is reconstructed using a system matrix. Distribution of emissions in a volume or image data is reconstructed from the detected emissions. The quantity or amount of uptake for each location (e.g., voxel) is estimated as part of the reconstruction in computed tomography. The SPECT imaging system estimates the activity concentration of an injected radiopharmaceutical or tracer for the different locations. In quantitative SPECT, the goal is to estimate the activity concentration in kBq/ml of the tracer (i.e., isotope) that was injected into and distributed within the patient.

The reconstruction is iterative and contains a model of the imaging formation physics as a pre-requisite of quantitative reconstruction. The image formation model includes the detected data (e.g., counts), the system matrix, isotope properties (e.g., corrected dose value), and biology. The system matrix represents mechanical properties of system, but may include other information (e.g., injection time and patient weight as represented by SUV).

Reconstruction includes a projection operator that is able to simulate a given SPECT system or SPECT class. Any now known or later developed reconstruction methods may be used, such as based on Maximum Likelihood Expectation Maximization (ML-EM), Ordered Subset Expectation Maximization (OSEM), penalized weighted least squares (PWLS), Maximum A Posteriori (MAP), multi-modal reconstruction, NNLS, or another approach.

The reconstruction uses the system matrix representing various aspects of the detection of the emissions, including modeling the imaging physics. The imaging physics includes aspects of the SPECT system, such as calibration of the SPECT system. The system matrix includes the detector sensitivity, such as the system specific sensitivity to the liquid radiotracer used in the patient. The system specific sensitivity (e.g., gamma camera planar sensitivity in SPECT) is used in the estimation of the activity concentration. The system specific sensitivity to the liquid radiotracer calculated in act 34 is used. Accordingly, the estimation is a function of the class standard sensitivities of act 30 and the measured system specific sensitivity to the calibrated or long-lived source of act 32. The corrected dose is included as part of the system matrix or as a separate isotope data used in reconstruction.

Using $S_{LR}$(SS) for activity concentration estimation by the reconstruction engine may produce activity concentrations that are accurate and free of or less responsive to camera specific or local dose calibrator specific variations. The reconstructed activity concentrations may be free or be less responsive to asynchronous clocks between the camera system and the dose calibrator.

In act 44, specific uptake values (SUVs) are calculated by the processor of the functional imaging system. The activity concentration represents the amount of uptake at each location. This amount of uptake is a measure of emitted radiation, so is not normalized for the radiation dose provided to the patient. As a result, comparing uptake from different times may not be useful unless the same does is provided. By calculating the SUV, uptake normalized for dose is provided, allowing comparison of different measures.

The SUV for each location or for some of the locations is calculated. The SUV is a function of the activity concentration for that location and the corrected dose value from act 40. The activity concentration is divided by the corrected injected dose value. Other functions may be used. For example, the SUV may be a function of the body mass or other physical characteristic of the patient. The uptake magnitude represented in the activity concentration is normalized for both dose and body mass.

Due to the cross-calibration, measurement of the system specific sensitivity to the calibrated, long-lived source, and use of measurements from both the long-lived and liquid radiotracer sources, the SUV may be compared over time or from different examinations. Different radiotracer dose and/or different detectors may be used. Where the different examinations use the approach of FIG. 1, the resulting difference in SUVs represents diagnostic or metabolic difference rather than difference due to variance in detector or dose. Quantification in functional imaging, such as SPECT, provides both accurate activity concentration and accurate SUVs.

Figure 2:
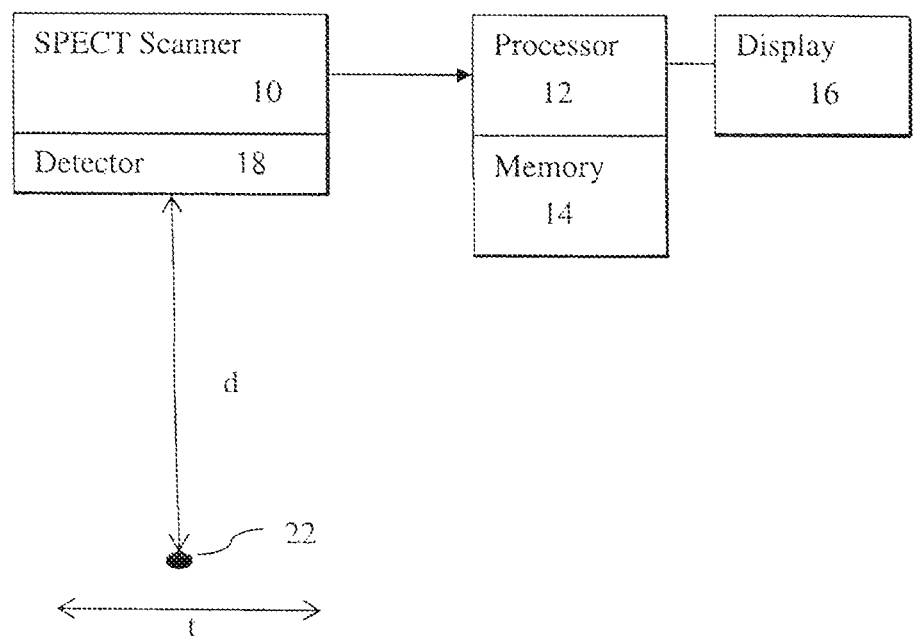
FIG. 2 is a block diagram of a system, according to one embodiment, for cross-calibration in functional imaging.

FIG. 2 shows a system 10 for cross-calibration in functional imaging. The system 10 includes an SPECT scanner 10, a processor 12, a memory 14, and a display 16. The processor 12, memory 14, and/or display 16 are part of the SPECT scanner 10 or are separate (e.g., a computer or workstation). Additional, different, or fewer components may be provided. For example, the system is a computer without the SPECT scanner 10. As another example, user input, patient bed, or other SPECT related devices are provided. Other parts of the system may include power supplies, communications systems, and user interface systems. In yet another example, a PET scanner or other functional imaging system is provided instead of the SPECT scanner 10.

The SPECT scanner 10 is a SPECT system. As a SPECT system, a detector 18 is provided. Other components may be provided, such as collimator. Any now known or later developed SPECT scanner 10 may be used.

The detector 18 is a gamma camera connected with a gantry. The gamma camera is a planar photon detector, such as having crystals or scintillators with photomultiplier tubes or other optical detector. The gantry rotates the gamma camera about the patient. During scanning of a patient, emission events are detected with the camera at different positions or angles relative to the patient. For sensitivity measurements from a point source 22 at a distance d from the detector 18, the gamma camera may be stationary.

The SPECT scanner 10, using the detector 18, detects emissions from the point source 22 for measuring system specific sensitivity. The point source 22 may be at any position in the 2D transverse direction, t, relative to the detector 18, but is preferably centered. The emissions are measured with the point source 22 at any distance, d.

The point source 22 is a long-lived, factory calibrated point source. Any size point source may be used, such as a 1 mm$^3$ vessel, with the long-lived radioisotope. The dose of the point source 22 is known with any degree of accuracy. The dose is measured at a factory with equipment having greater accuracy than used in labs providing liquid radiotracers. Any now known or later developed point source may be used. The point source 22 is used as a calibration radiotracer source. The long-lived point source 22 is for calibrating. The point source 22 is positioned relative to the detector 18 for measuring detector or system specific sensitivity to the point source.

The SPECT scanner 10 may include a timer. The timer measures a period from activation of detection through to reaching a number of counts. The emission events detected by the detector 18 are counted over time to calculate the sensitivity. The SPECT scanner 10, using the processor 12 or another processor, is configured to measure the system specific sensitivity of the detector 18 to the long-lived point source 22.

For imaging uptake in a patient, the detector 18 detects emissions from the patient. The emissions occur from any location in a finite source (i.e., the patient). The radiotracer in the patient migrates to, connects with, or otherwise concentrates at specific types of tissue or locations associated with specific biochemical reactions. As a result, a greater number of emissions occur from locations of that type of tissue or reaction. For example, the radiotracer is designed to link with locations of glucose uptake, fatty acid synthesis, or other metabolic process.

The SPECT scanner 10, using the processor 12 or another processor, is configured to reconstruct the imaged volume by applying a system matrix to the detected data. Any reconstruction may be used to estimate the activity concentration in the patient. The processor 12 is used to perform the reconstruction, or the SPECT scanner 10 has another processor that performs the reconstruction. The SPECT scanner 10 accesses the detected emission events from the memory 14 or buffers to reconstruct. The system matrix includes a system specific sensitivity for the liquid radiotracer provided to the patient. This sensitivity is used for the reconstruction. The reconstruction also uses a dose value for the radiotracer applied to the patient.

The processor 12 is a general processor, digital signal processor, graphics processing unit, application specific integrated circuit, field programmable gate array, digital circuit, analog circuit, combinations thereof, or other now known or later developed device for processing emission information. The processor 12 is a single device, a plurality of devices, or a network. For more than one device, parallel or sequential division of processing may be used. Different devices making up the processor 12 may perform different functions, such as one processor (e.g., application specific integrated circuit or field programmable gate array) for reconstructing and another for calculating a cross-calibration function and/or system specific sensitivity to a radiotracer to be injected. In one embodiment, the processor 12 is a control processor or other processor of SPECT scanner 10. In other embodiments, the processor 12 is part of a separate workstation or computer.

The processor 12 operates pursuant to stored instructions to perform various acts described herein, such as calculating of act 34, counting or controlling the counting and calculation of the system specific sensitivity to the point source 22 for the measurement of act 32, receiving the dose calibrator sensitivity in act 36, determining the cross-calibration factor of act 38, correcting the dose of act 40, estimating activity concentration of act 42, and/or calculating uptake values of act 44. The processor 12 is configured by software and/or hardware to perform, control performance, and/or receive data resulting from any or all of the acts of FIG. 1.

In one embodiment, the processor 12 is configured to reduce variability due to dose and detector sensitivity of uptake values and activity concentration output by the functional imaging system (e.g., the SPECT scanner 10) for a patient. The processor 12 is configured to reduce variability as a function of a class standard sensitivity to a liquid radiotracer source and a system specific sensitivity to the calibration radiotracer point source 22. The class standard sensitivities to a liquid radiotracer and to a long-lived point source are loaded from memory 14 or received by transfer. These sensitivities provide a ratio that may be used with the measured system specific sensitivity to a same or different point source 22 for calculating, by the processor 12, the system specific sensitivity to the liquid radiotracer. Using dose calibrator liquid radiotracer sensitivity, the processor 12 is configured to calculate a cross-calibration or dose correction factor. The sensitivity is input to the processor 12 with user interface, loaded from memory 14, or transferred over a network. The correction factor and calculated system specific sensitivity may reduce variability in reconstruction and/or calculation of specific uptake values.

The processor 12 is configured to correct the input dose of the liquid radiotracer provided to the patient. The correction factor is multiplied with the dose. Based on this corrected dose, the processor 12 is configured to calculate SUVs. The SUV at one or more locations are calculated by normalizing the activity concentration with the corrected dose. The resulting SUVs have less variability due to the system and/or dose, so more likely represent changes in metabolic function of the patient.

The detected emission events, other functional information, or other scan data is stored in the memory 14. The data is stored in any format. The memory 14 is a buffer, cache, RAM, removable media, hard drive, magnetic, optical, database, or other now known or later developed memory. The memory 14 is a single device or group of two or more devices. The memory 14 is part of SPECT scanner 10 or a remote workstation or database, such as a PACS memory.

The memory 14 may store data at different stages of processing, such as counts, time to reach a count, raw data representing detected events without further processing, filtered or thresholded data prior to reconstruction, reconstructed data, filtered reconstruction data, system matrix, projection data, thresholds, an image to be displayed, an already displayed image, or other data. The memory 14 or a different memory stores class standard sensitivities loaded into or provided to the SPECT scanner 10. The memory 14 or a different memory stores the cross-calibration factor and/or any of the sensitivities. For processing, the data bypasses the memory 14, is temporarily stored in the memory 14, or is loaded from the memory 14.

The memory 14 is additionally or alternatively a non-transitory computer readable storage medium with processing instructions. The memory 14 stores data representing instructions executable by the programmed processor 12. The instructions for implementing the processes, methods and/or techniques discussed herein are provided on non-transitory computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The display 16 is a CRT, LCD, plasma screen, projector, printer, or other output device for showing an image. The display 16 displays an image of the reconstructed functional volume, such as showing activity concentration as a function of location. The uptake function of the tissues of the patient is represented in the image. Multiplanar reconstruction, 3D rendering, or cross-section imaging may be used to generate the image from the voxels of the reconstructed volume. Alternatively or additionally, any quantities derived by the processor 12 may be displayed, such as SUVs and/or change in SUV. Other quantities may be determined, such as average SUV or activity concentration for a region, maximum SUV, peak SUV in a predetermined unit volume, variance in activity concentration, or total SUV.

Application of or Framework for Cross-Calibration

The cross-calibration of FIGS. 1 and 2 is implemented in any of various ways. FIGS. 3-11 show example frameworks for implementing cross-calibration. These frameworks for calibration of a SPECT system can be used for later dose correction in imaging a specific patient. Tables of sensitives and cross-calibration factors are generated for unique combinations of well counter and other options. For use with a particular patient, the sensitivities and cross-calibration factor for a given situation are loaded from the tables and used in dose correction and reconstruction.

Figure 3:
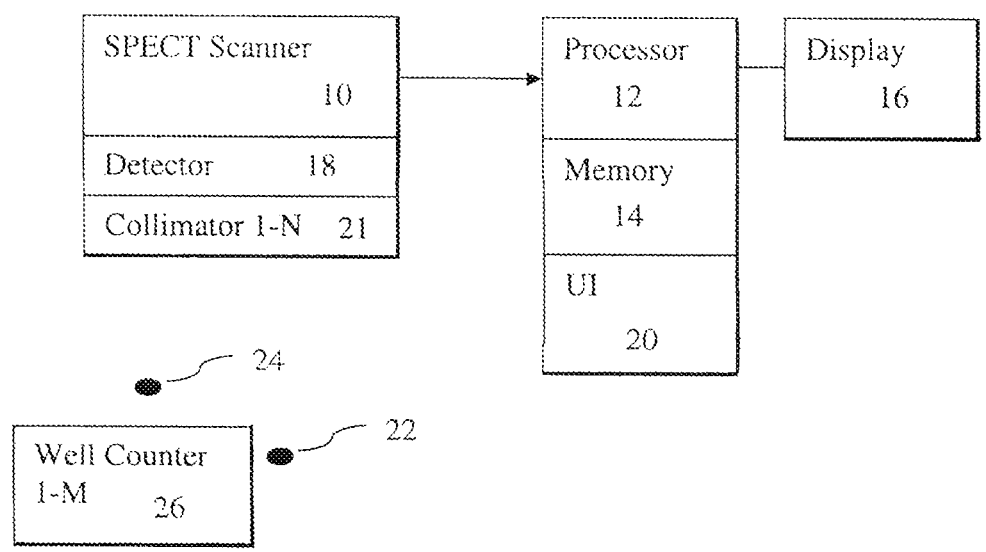
FIG. 3 is a block diagram of a system, according to one embodiment, for application of cross-calibration in functional imaging

FIG. 3 shows one embodiment of a system for application of cross-calibration in functional imaging quantification. The system of FIG. 3 is the system of FIG. 2, but presented in a different context. The system implements the framework, so is associated with various imaging options.

The functional imaging system is provided for use by an entity, such as research team, for a clinical study, by hospital physicians, or other organization. In the embodiment shown, the functional imaging system is a SPECT system 10. This SPECT system 10 is at a facility, such as a research institute, clinical study location, or hospital.

The SPECT system 10 has one or more detectors 18, such as two detectors 18 (e.g., two planar gamma cameras). Different detectors 18 may have different sensitivities and/or result in different cross-calibration factors. The SPECT system 10 includes one or more collimators 21. Different collimators 21 may be used in different situations. The different collimators 21 may result in different sensitivities of the detector 18. For a given scan, one collimator 21 may be selected and used while other collimators 21 are not. The sensitivity and cross-calibration may be different for different detectors and/or collimators.

The facility has one or more well counters 26 (e.g., dose calibrators). The well counters 26 measure the dose to be provided to a patient. The assay sent for injection into a patient and/or the residual left after injection of the patient may be measured. With multiple well counters 26 available, a given well counter is used to measure a given dose. Different well counters 26 or the same well counter 26 may be used at different times. Due to age, design, and/or manufacture, different well counters 26 may provide different dose values for a same dose. The sensitivity and cross-calibration may be different for different well counters.

A plurality of isotope sources 22, 24 are provided. The isotope sources 22, 24 are liquid radiotracers, factory calibration sources, or both. The different isotope sources 22, 24 use different isotopes, with corresponding different energy windows. One or more of the isotope sources 22, 24 may include an isotope with multiple energy windows, such as 2-8 energy windows. The sensitivity and cross-calibration may be different for different isotopes and/or energy windows.

Other options effecting sensitivity and/or cross-calibration may be available. For scanning a particular patient, one of each option is selected and used. For calibration, different combinations of the available options may be used to calibrate the SPECT scanner 10 for any given combination used for a patient.

The user interface 20 is the display 16 or other output and a user input device. Any user input device may be used, such as a keyboard, mouse, track ball, track pad, touch screen, sliders, buttons, or knobs. Any user interface arrangements may be used, such as drop down menus, text entry fields, selection boxes, tabs, menus, or other now known or later developed user interface options for user interaction with the SPECT scanner 10. In one embodiment, the user interface 20 is configured by software executed by the processor 12 for selection of one energy windows for a photo-peak window and selection of another energy windows for a scatter window.

The processor 12 is a processor of the functional imaging system, but may be a processor of a separate computer or server. In one embodiment, the framework for applying the cross-calibration is implemented by software, hardware, or firmware on the SPECT scanner 10. By building the framework directly on a SPECT scanner 10, the framework is directly deployed to clinical site. SPECT scanners 10 being used as research boxes, used for clinical operation, or other uses of quantitative SPECT provide the framework without having to port data to other systems and/or without arranging for interaction between different systems.

The processor 12 is configured to determine a sensitivity responsive to a measure by the well counter 26. The sensitivity is responsive to various options, such as detector 18, collimator 21, isotope, energy window, dose, and/or well counter 26. Each unique combination of options may have a different sensitivity. For calibration, sensitivities are determined for multiple different unique combinations.

The sensitivity is determined as discussed above for the cross-calibration. For example, acts 30, 32, and 34 of FIG. 1 are performed. By repeating the acts for different combinations, a table of system-specific sensitivities are calculated. The table includes the sensitivity linked to the combination of options.

The processor 12 is configured to determine a cross-calibration between two isotope sources 22, 24. The cross-calibration factor is determined as discussed above for cross-calibration. For example, acts 30-38 of FIG. 1 are performed. The sensitivity as calculated is used to determine the cross-calibration factor, so the table of sensitivities may be searched to provide the information for determining cross-calibration.

The cross-calibration is responsive to various options, such as the well counter 26 used, the isotopes, the energy windows of the isotopes, the detector 18, and/or the collimator 21. The cross-calibration, being a function of the sensitivity, is specific to the well counter 26. A different well counter 26 used to measure dose may have a different cross-calibration factor. Each unique combination of options may have a different cross-calibration factor. For calibration, cross-calibrations are determined for multiple different unique combinations.

The processor 12 is configured to search a table of cross-calibrations. When being used to scan a particular patient, the unique combination of options for that scan is identified, such as by controlling the SPECT scanner 10 and/or inputting selections on the user interface 20. Based on the unique combination of options (e.g., well counter 26 used to measure dose), the cross-calibration is found in the table of cross-calibrations. The processor 12 uses the cross-calibration to correct a patient dose measured by the well counter 26. Based on the selection of the well counter 26, the patient dose measured by the well counter 26 is corrected.

The correction uses the calibration factor. For example, the processor 12 performs act 40 of FIG. 1. Using the calibration table for cross-calibration factors, the correction appropriate for a given arrangement of the SPECT scanner 10, well counter 26, and isotope is performed.

In another embodiment, the sensitivity for the combination or arrangement being used for a patient is located from the table of sensitivities. The estimation of the activity concentration of act 42 of FIG. 1 is performed using the looked-up sensitivity. Where the isotope has multiple energy windows, the sensitivity and/or cross-calibration are determined specific to the photo-peak and scatter windows selected from those multiple energy windows.

The memory 14 includes instructions for the processor 12 and/or the SPECT scanner 10. The memory 14 includes instructions, as discussed above for FIG. 2, for application of cross-calibration in the SPECT system.

Alternatively or additionally, the memory 14 includes input values from the user interface 20 and/or stores the sensitivity and cross-calibration tables generated by the processor 12. The various unique combinations, such as all or a sub-set of possible unique combinations, and corresponding determined sensitivities and/or cross-calibrations are stored. The different combinations are linked with one or more well counters 26. The well counter 26 is one of the options for the unique combinations.

Figure 4:
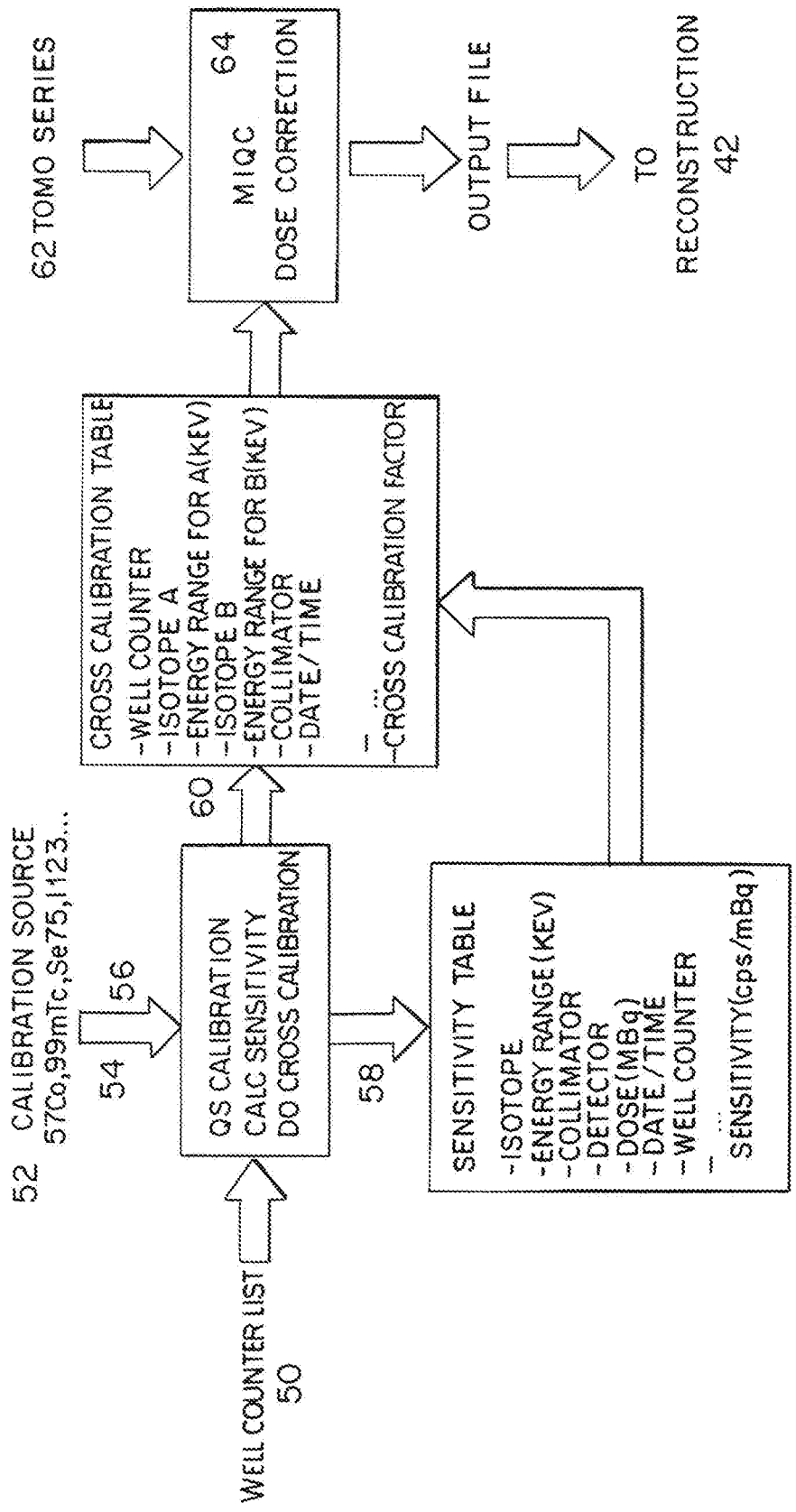
FIG. 4 is a flow chart diagram of one embodiment of a method for application of cross-calibration in functional imaging.

FIG. 4 shows one embodiment of a method for application of cross-calibration for a quantitative SPECT system. The method implements a framework provided by the SPECT system, such as by software executed by a processor or processors of a SPECT scanner. The executed instructions perform various tasks, including computing the system sensitivities for a given isotope and collimator, derive the cross-calibration factors for specified well counter(s) using pairs of isotopes, and correct the injected dose in quantitative applications by applying the system specific cross-calibration factors. Each of these tasks is operated as a separate module, but may be combined or further separated.

Additional, different, or fewer acts may be provided. For example, act 56 is not provided where the isotopes have one energy window. As another example, acts 62, 64, and 42 are not provided where the method is for populating the tables as part of calibration. In yet another example, acts 50-60 are not provided where the method is for using the sensitivity and/or cross-calibration tables in acts 62, 64, and 42 without calibrating to populate the tables.

The acts are performed in the order described below, numerical order, or another order. For example, acts 50, 52, and 54 are performed in any order.

The method is performed by the system of FIG. 3 or a different system. For example, the user interface is used to input the source isotopes in act 52, the well counter selection of act 50, selection of energy windows of act 56, and other options for calibration. The processor performs acts 54, 58, and 60 with information from the well counter, SPECT scanner (e.g., detector using a given collimator), isotope information from the memory, and/or information for other options. Different devices or components may be used to perform different acts.

As discussed above, the SPECT system is provided at a facility. The SPECT system includes one or more detectors configured to operate with different collimators to detect emissions from different liquid radiotracers with different injected dosages measured by different well counters. The SPECT system at a given facility is provided with different options for collimators, isotopes, energy windows, and/or well counters available at the facility.

Different liquid radiotracers and corresponding isotopes used in the radiotracers may be used with the SPECT system. Similarly, different factory calibration sources and corresponding isotopes used in the factory calibration sources may be used with the SPECT system.

The available isotopes may be standard isotopes. For example, the FDA approves particular isotopes. These isotopes are standardized, such as being available with assigned code values following the DICOM standard. The isotopes and their characteristics (e.g., energy window(s) and half-lives) are known and used in many facilities. Some or all of the available isotopes may not be standardized. For example, LU177 is standard in Europe, but not standard in the US (e.g., not approved). Experimental, research, or clinical study facilities may use non-standard isotopes. A user defines the isotopes and their characteristics. This custom isotope information may be saved in or imported to a database and/or added to a list of available isotopes.

For creation of the sensitivity and/or cross-calibration tables, various information is received. The available options provided at the facility are input. A sub-set of available options may be input in other embodiments. The particular ones of the options for any given combination are selected to populate the sensitivity and cross-calibration tables for that combination. Alternatively, the technician enters each given combination for calibration.

In act 50, the user interface receives input identifying at least one well counter. The well counter is used to determine a dose used for calculating the sensitivity, such as determining dose of a calibrated source and/or a liquid radiotracer source. Different well counters may be used for measuring different sources. Similarly, different well counters may be used for measuring an assay (i.e., dose provided for injection) and residual doses (i.e., dose not injected or remaining after injection). For calibration, there may be on residual dose as the well counter measures the assay, which is used as a point source without injection. The well counter(s) and corresponding dose information are input for cross-calibration.

In act 52, the user interface receives input of an identity of one or more radioactive sources. The sources are identified. Alternatively, the isotopes used in the sources are identified. For creating the tables, a factory calibration source or isotope and a liquid radiotracer source or isotope are input.

Figure 5:
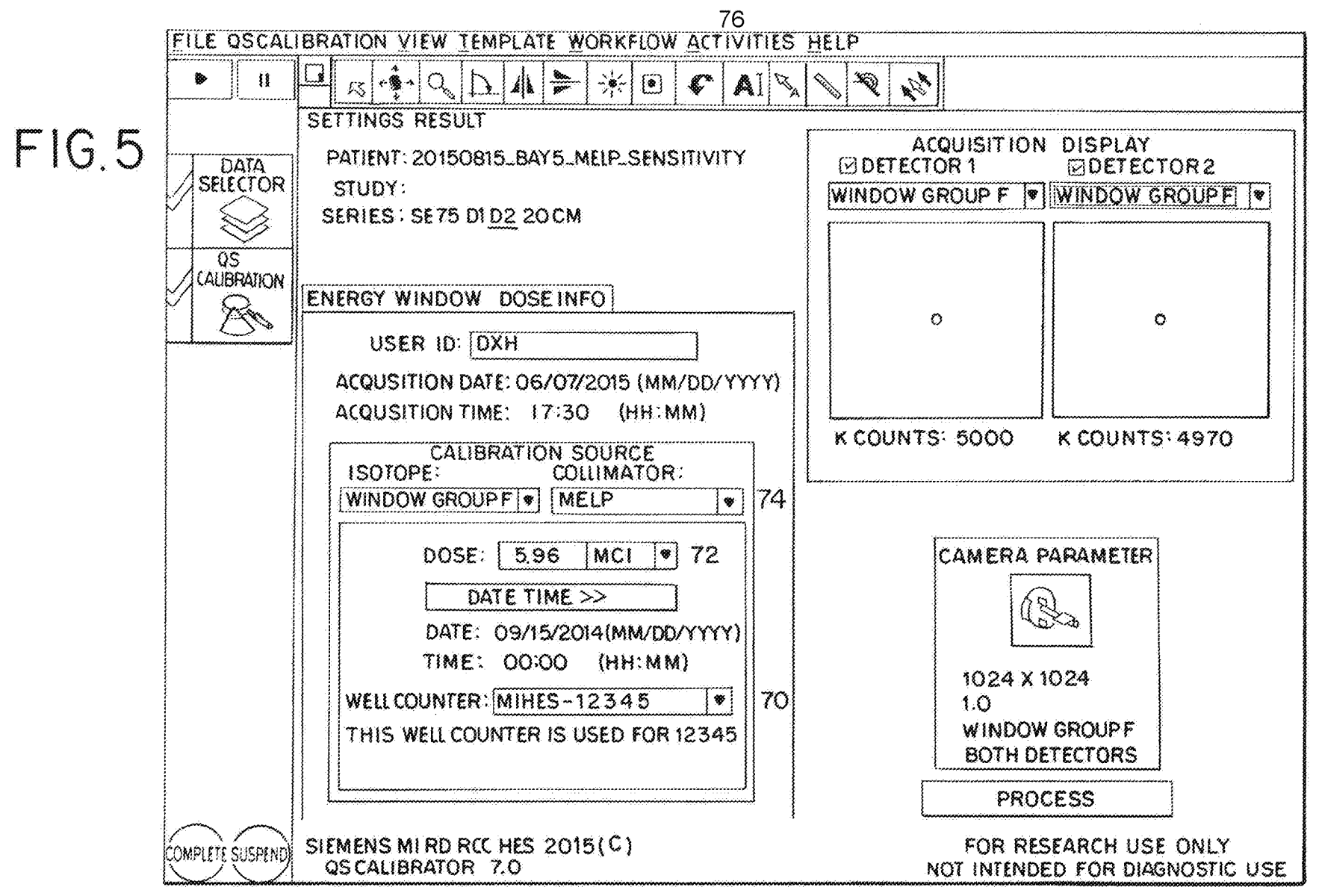

FIG. 5 shows one example display 76 for a user interface for inputting the isotope, dose and well counter information. In this example, the isotope is input with identification of the collimator at 74. The isotope and collimators are selected from a drop down. The dose for the liquid radiotracer is input in a text field at 72. Different units may be assigned using a drop down selection. At 70, the well counter used to measure the input dose is selected from a drop down. Different tabs, sections, and/or selections may be provided for different isotopes and/or doses.

Other types of input and/or dose information to be input may be used, such as selecting a dose as an assay or residual dose. Other user interface arrangements may be provided.

The right side of FIG. 5 also shows two projection images of acquisition by the SPECT scanner for the radiotracer source as a point source and dose input. Two images are provided with two different counts using two detectors. More or fewer detectors and corresponding images may be provided. In alternative embodiments, the images of the point source and/or corresponding counts are not provided on the display.

In act 54, the processor searches for characteristics of the identified radioactive sources. The framework recognizes any isotopes proper for medical imaging. One or more lists or types of isotope information are searched. In one embodiment, a standardized list of sources is searched. This is the first search, but may be performed in parallel or after other searches. The standardized list includes code values following a standard, such as the DICOM standard. The standard is based on a multi-party or industry agreement and/or based on government approval. For example, the DICOM standard is an industry standard that includes code values for isotopes approved by the FDA.

Another list is also searched or is searched if the input isotope is not in the standardized list. A SPECT scanner may be used for clinical study, research, or other purposes that result in use of an isotope not included in the standardization. This custom list is of un-standardized radioactive sources. If the isotope is not yet standardized, a customer pre-set list is searched.

The custom list is created by pre-defining any strings for a particular isotope. FIG. 6 shows an example list 78 with five custom isotopes. The strings 80 are alphanumeric text that may be used as labels for the isotope. In the example of FIG. 6, three different labels are entered for each isotope, but more or fewer labels or strings may be used for one, some, or all of the isotopes. This list is created as a new isotope is used and/or is created prior to searching. The list is configurable (e.g., which isotopes to include, what strings, to use, and what characteristics to link to each isotope). The user may add any strings for a particular isotope that DICOM has not yet standardized.

The custom list is searched separately from the standard list. Alternatively, the lists are combined so that the common list is searched for the identified isotope.

Once the isotope is found in the list, the characteristics of the isotope are identified. The list includes or links to one or more characteristics. For example, the half-life and energy windows for the isotope are included. For none, one, or more isotopes, the characteristics include a plurality of energy windows. A given isotope may have more than one energy peak, so multiple energy windows exist for that radioactive source. Additional, different, or fewer characteristics may be included.

In act 56, the user interface receives user selection of energy windows for the radioactive sources. Where the isotope has only one energy window, the selection may be automatic by the processor. Where the isotope has more than one energy window, the selection may be automatic to one of the windows as a default. The processor selected window is displayed to the user as well as other options.

Alternatively, the available windows for the isotope are displayed on the user interface for selection by the user. Any display format or selection function may be used. Where multiple energy windows are available, one window may be selected as a main, primary, or photo-peak energy window, and another window may be selected as a scatter window. The framework allows cross-calibration for any combinations of the main energy window and the scatter windows. This is useful for two isotopes that have multiple energy windows. The located isotope characteristics are used to populate and display a list of energy windows or other representation of the energy distribution for the isotope.

Figure 7:
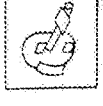
FIG. 7 illustrates an example user interface for selecting energy windows for isotopes with multiple energy windows.

FIG. 7 shows one example user interface display 82 for receiving user selection of energy windows. The user can select which range shall be the main photo peak and which range(s) shall be the scatter(s). In FIG. 7, two lists 84 of energy distribution (e.g., energy windows) are displayed, one for a reference isotope source (e.g., reference liquid radiotracer isotope) and the other for a current isotope source to be calibrated (e.g., for scanning a patient). Where the energy distributions are provided for calibration, there may be only one list or isotope energy distribution and/or an energy distribution may be provided for the factory calibration source. In the example of FIG. 7, the reference isotope source is selenium 75 where the primary window range is selected as (121, 148) key, and the two scatter windows are selected as (148,175) key and (94,121) key from the list of six energy windows. The energy distribution for the current isotope source to be calibrated is for lutetium 177, which has five energy windows with one selected for the primary and one for the scatter. In this example, the user selects the first and the second energy ranges as the main and scatter windows for cross calibration, respectively. Other user interfaces for manual or user-based selection of energy windows may be provided.

In acts 58 and 60, tables of sensitivities and cross-calibration factors are generated. These tables are generated during calibration of the SPECT system at the facility. Calibration prior to installation at the facility may be used. Once at the facility, the SPECT system is calibrated on a periodic basis. For example, monthly, bi-monthly, semi-annually, or after a given number of uses, the SPECT system is calibrated by a technician.

Using software, firmware, and/or hardware of the SPECT scanner, the SPECT scanner is calibrated for use. The calibration function, including the user interface for receiving information in acts 50, 52, and 56, is integrated into or built directly in the SPECT scanner. A program module is used by the technician to generate the tables.

The system-specific sensitivity for the SPECT system and the cross-calibration factor relating radioactive sources are determined and saved in the tables. While two tables are shown, one table or a network of interrelated tables may be used.

As discussed above for FIGS. 1 and 2, the sensitivity and cross-calibration factor are determined based on various options, including characteristics of the isotopes. Other options effect the sensitivity and/or cross-calibration factor. Each sensitivity and cross-calibration factor are determined for a given combination of options. For example, the sensitivity and cross-calibration factor are determined for a specific one of two or three well counters, a specific one of four collimators, a specific one of two detectors, two particular isotopes out of many, and specific energy windows (e.g., both primary and scatter) in combination.

To generate the table, different combinations are used. Any number of unique combinations of options may be used. A system-specific sensitivity and cross-calibration factor are determined for each of a plurality of different option combinations. The technician may select a sub-set of unique combinations to use or may generate the tables to cover all possible combinations. For example, the dose level may be restricted to a few common doses and the closest dose combination is used for a given patient. As another example, sensitivity and/or cross-calibration factor are not determined for any combinations including a particular isotope, energy window, and/or collimator, such as where that particular one is not used or scheduled to be used.

The generated tables provide sensitivities and/or cross-calibration factors for a plurality of different combinations of options. For example, sensitivities and cross-calibration factors are generated for each of a plurality of different well counters with the other options being the same or different (e.g., collimator #1 used for both). For each well counter, sensitivities and cross-calibration factors are generated for each of a plurality of combinations of specific ones of energy windows, collimators, detectors, isotopes, and/or other options.

In act 58, the processor generates a sensitivity table of system-specific planar sensitivities. As discussed above in FIG. 1 for act 34, system-specific planar sensitivities are generated from class planar sensitivities to the isotopes and a factory calibration source and system specific planar sensitivity to a factory calibration source.

Figure 8:
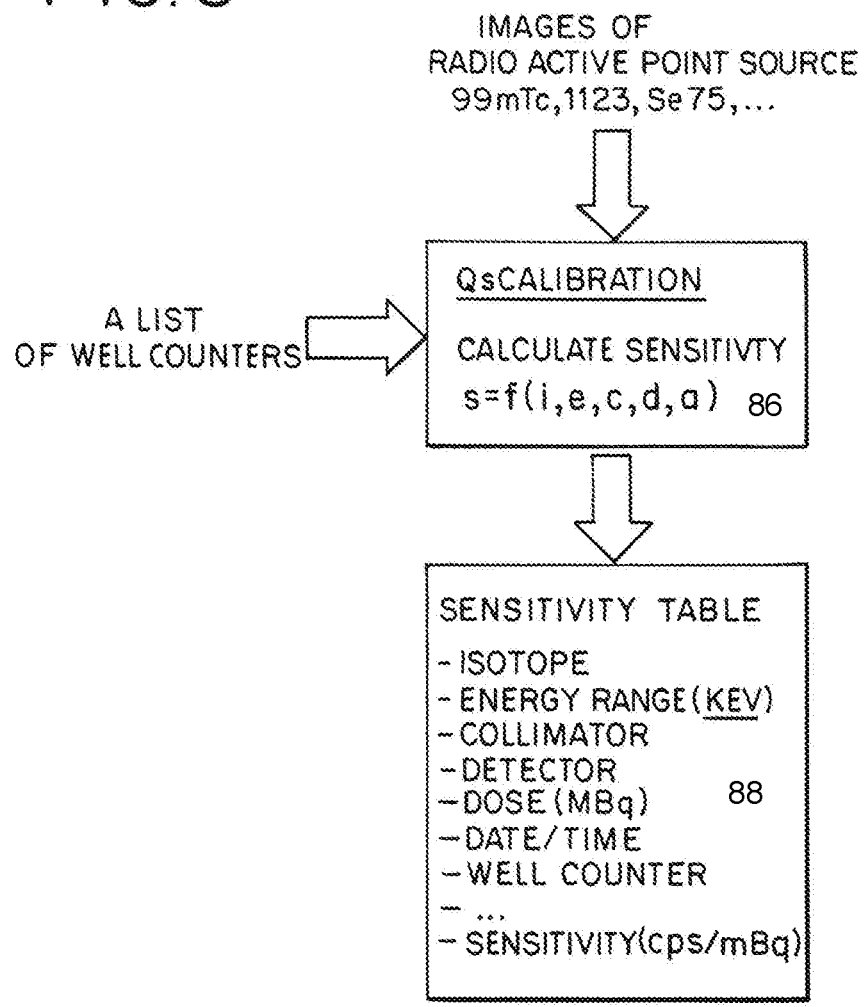
FIG. 8 shows generation of a sensitivity table.

Referring to FIG. 8, the QsCalibration activity or software process calculates system sensitivities for a given isotope and collimator. The well counter and other option information are input with images or scan data used to calculate 86 the sensitivity. The results are saved in a table 88 with the option information, such as the isotope, energy range, collimator, detector, dose of the liquid radiotracer, and the well counter used to measure the dose. The sensitivity table is generated to include one system specific planar sensitivity for each unique combination of isotope, energy of isotope, collimator, detector, dose, and/or well counter. Where one of the isotopes includes multiple energy windows, the option information includes the main energy window and/or scatter energy window used to generate the sensitivity.

Figure 9:
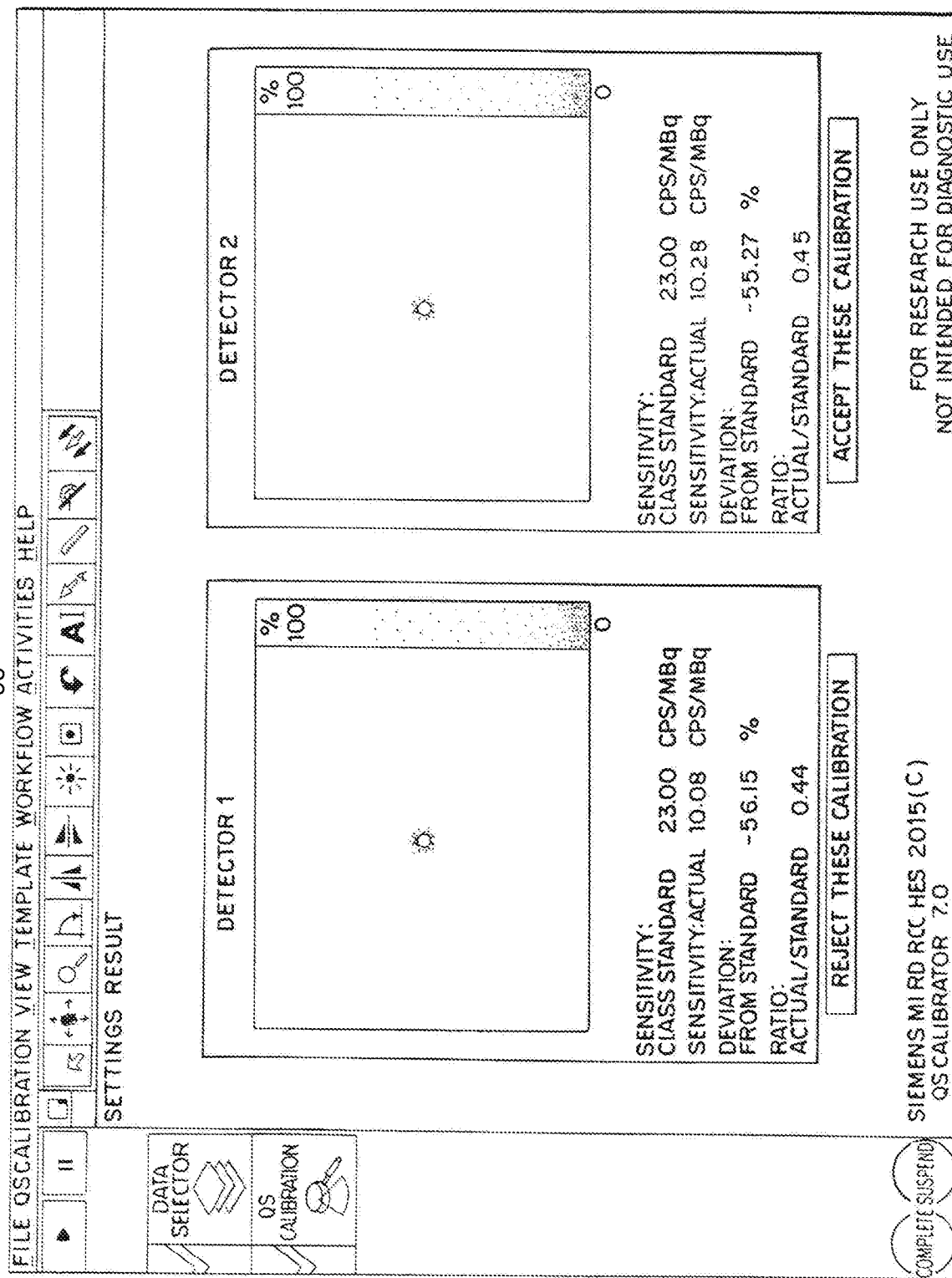
FIG. 9 illustrates an example user interface for outputting sensitivity information.

FIG. 9 shows an example user interface display 90 showing scan image or data used to calculate sensitivity for two detectors. The sensitivity, class standard sensitivity, deviation from the class standard, and ratio with class standard are provided. Additional, different, or less information may be provided, such as displaying just the system-specific planar camera sensitivities for each of the combinations of options calibrated by the technician. In another embodiment, the sensitivity table is displayed as the table is created or after creation. Alternatively, the sensitivities are not displayed.

For sensitivity measurement, the sensitivity (S) is measured for the combinations of the isotope (i), the energy (including scatters) of the isotope (e), the collimator (c) used, the detector (d), and the dose ($\alpha$). To emphasis these dependencies, the sensitivity is written in functional notation as S=f(i, e, c, d, α). As shown in the FIG. 8, the static projection images (typically a point source, see FIG. 9) are used to compute the sensitivity and store the result in a sensitivity table. The options include user selection of a particular well counter from a list of available well counters specific to the clinical site.

In one embodiment, the sensitivity s=f(i, e, c, d, α) is calculated as follows. $C_p$=the total counts of the projection image in the photo peak energy window, $C_s$=the total counts of in the scatter energy window(s), $A_0$=injected dose in MBq, $T_{1/12}$=the half-life of the isotope in seconds, $\lambda=\ln(2)/T_{1/12}$, T=acquisition duration in seconds, $A=[A_0/(\lambda T)](1-\exp\{-\lambda T\})$, and then $S=(C_p-0.5C_s)/(AT)$(cps/MBq). Other calculations may be used. The calculation is repeated for different unique combinations of the options to populate the table.

In act 60, the processor generates the cross-calibration table of cross-calibration factors. Cross-calibration factors are generated for each unique combination of isotope, collimator, energy of the isotope, detector, and/or well counter. Other combinations of options may be used. To derive the cross-calibration factors for each well counter in the well counter list, the output is saved in the cross-calibration table.

Figure 10:
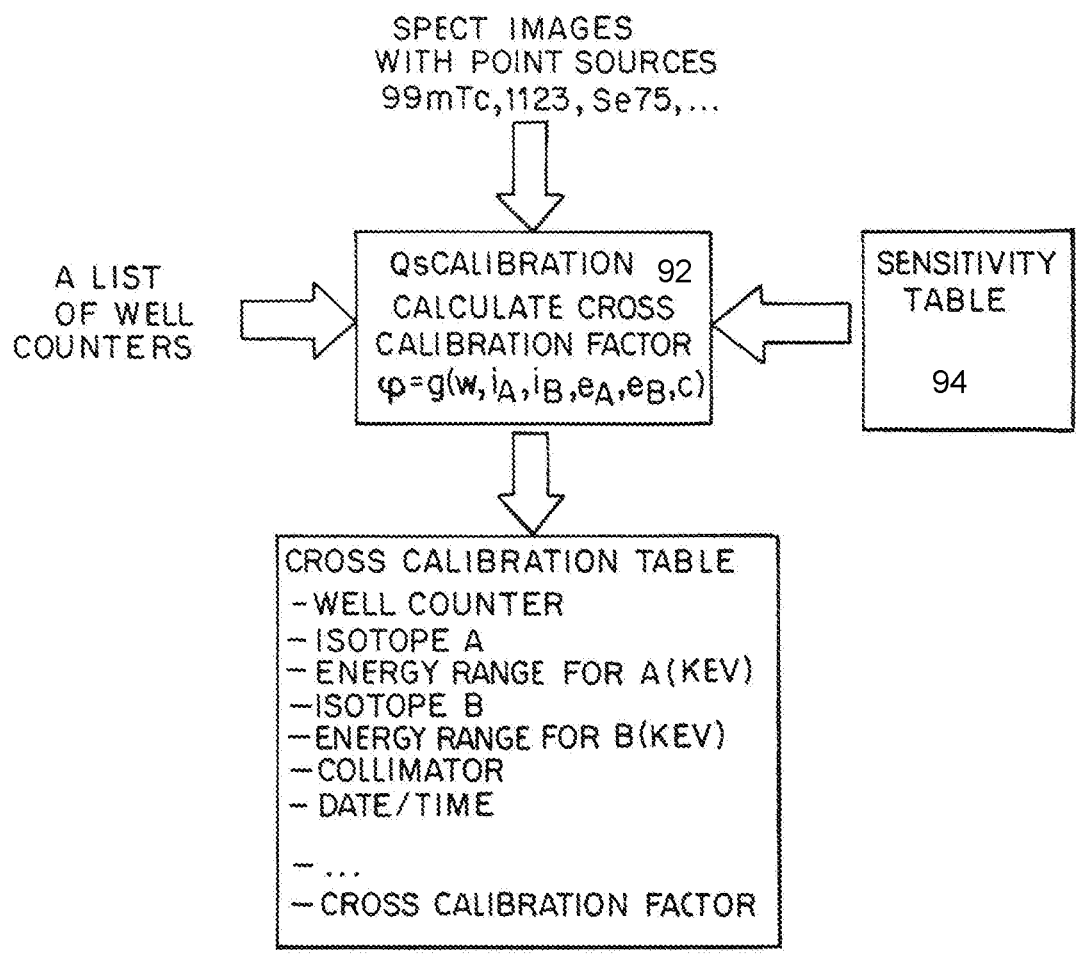
FIG. 10 shows an example generation of a cross-calibration table.

FIG. 10 shows an example where the inputs include the options, such as the well counters, the SPECT scan data for the isotopes, and the sensitivity table 94. Other inputs may be used. The QsCalibration process or program module integrated in the SPECT scanner performs the cross-calibration calculation 92.

As shown in FIG. 1, to create the cross-calibration table, the information from the sensitivity table is accessed or used. The cross-calibration factors are a function of the system specific planar sensitivities. The sensitivity calculation for a given combination of options is run first, and then the cross-calibration factor is calculated. The sensitivity is looked-up from the sensitivity table to calculate the cross-calibration factor. This process is repeated for each unique combination of options. Alternatively, the sensitivity table is populated for various combinations, and then the cross-calibration table is generated for the various combinations.

To emphasize the dependence of the cross-calibration factor φ on the various options, such as the well counter, the two isotopes, and the collimator, the cross-calibration factor is provided in functional notation as $\varphi=g(w, i_A, i_B, e_A, e_B, c)$, where w is a well counter, $i_A$, $i_B$ denote two isotopes A, and B, with energy $e_A$ and $e_B$, respectively, and c denotes the collimator.

Figure 11:
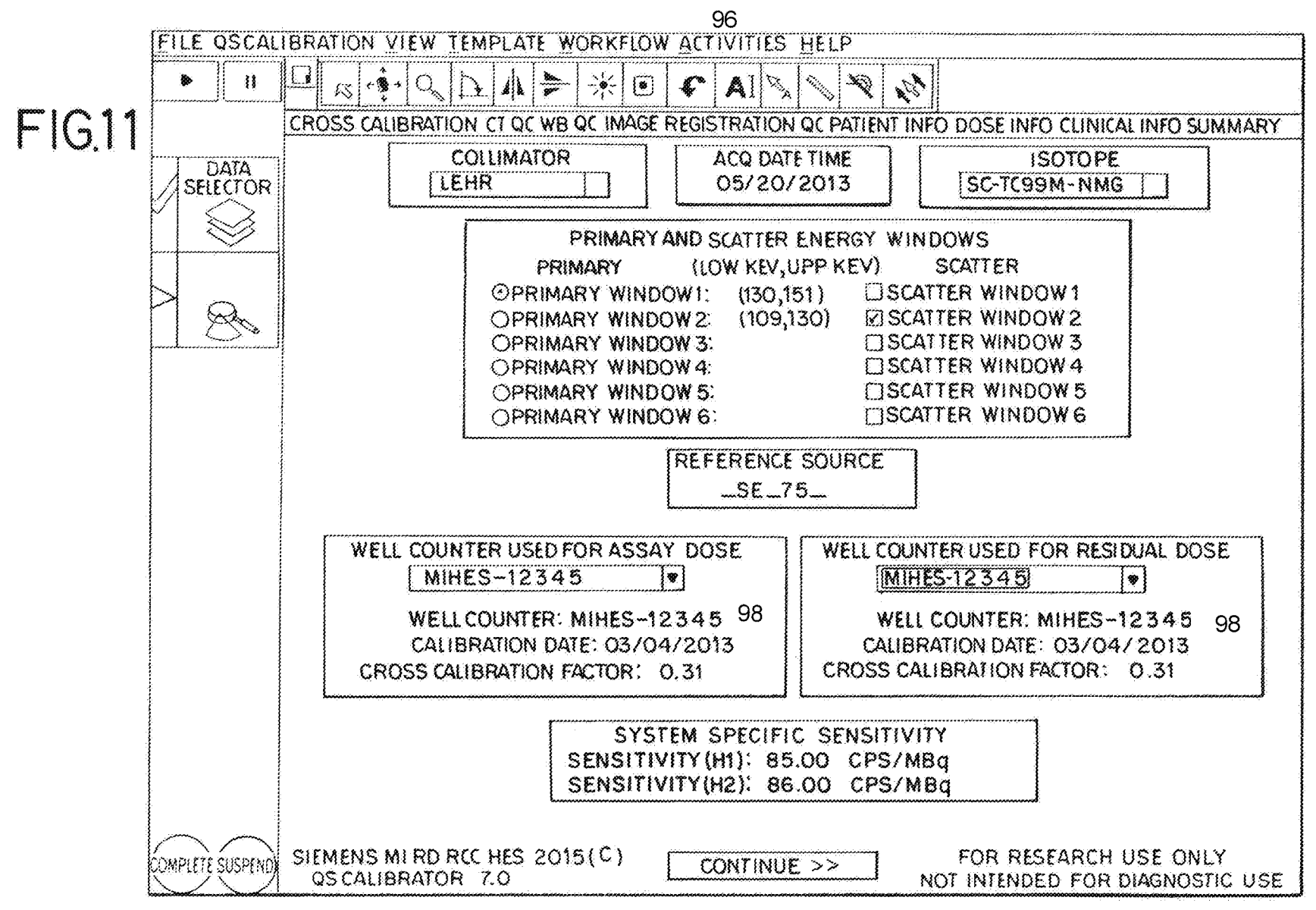

FIG. 11 shows an example user interface display 96 for the technician. The user interface is for inputting information to generate the cross-calibration for populating the table and/or for displaying the results of the cross-calibration calculation. In this example, the sensitivities for two detectors in the unique combinations (w, $i_A$, $i_B$, $e_A$, $e_B$, and c) are loaded and displayed. The output 98 is the cross-calibration factor for each of the detectors. The cross-calibration factors are saved in the cross-calibration table with the option information (e.g., the specific well counter identifier, the two isotopes and their emission energies, and the collimator used). The resulting system specific cross-calibration table is then available for use in actual patient acquisition to correct the injected dose.

To compute the cross-calibration factor, act 38 of FIG. 1 is performed. In one example, the isotope $i_A$ is the precision cross calibration reference source (e.g., factory calibration source), and isotope $i_B$ is the variable clinical application source (e.g., liquid radiotracer). The factory default is a set of pre-determined class standard measurements, while system specific is measurement done on each specific system in a particular clinical site. The cross calibration factor $\varphi=g(w, i_A, i_B, e_A, e_B, c)$ is calculated as follows. For k=1,2, denote, $_AS_{f,k}$,=the factory default sensitivity for isotope $i_A$ with energy $e_A$, for detector k, $_BS_{f,k}$=the factory default sensitivity for isotope $i_B$ with energy $e_B$ for detector k, $_AS_{m,k}$=the system specific sensitivity for isotope $i_A$ with energy $e_A$ for detector k, and $_BS_{m,k}$=the system specific sensitivity for isotope $i_B$ with energy $e_B$ for detector k. The calculation forms the following ratio for each detector: $r_k=(_BS_{m,k}\, _AS_{f,k})/(_AS_{m,k}\, _BS_{f,k})$, k=1, 2. The cross-calibration factor is the average of these ratios over the two detectors, $\varphi=(r_1+r_2)/2$. Other computations for the cross-calibration factor may be used, including maintaining separate cross-calibration factors for the two detectors.

Referring again to FIG. 4, the populated tables created during calibration are available for use with the SPECT scanner for scanning objects, such as patients. The tables are stored in a memory that is part of or accessible to the SPECT scanner. The SPECT scanner implements software or programming to access the tables, scan the object, correct for dose, and reconstruct the object from the scan. The module or process MiQC in the example of FIG. 4 is integrated with the SPECT scanner and performs the dose correction. To apply one of the cross-calibrations to a specific application, such as a tomo acquisition, the activity MiQC is instantiated. Activity concentration estimation, reconstruction, uptake calculation or other quantitative SPECT imaging is likewise performed by the SPECT scanner using the corrected dose information and sensitivity.

In act, the SPECT scanner, processor, and/or user interface receive identities of options to be used for scanning the object. For example, the identities for a particular one or more of the well counters used to measure the dose are received. One well counter for both or two well counters are identified for measuring the assay dose and the residual dose to determine the injected does. The given collimator, detector or detectors, dose, and isotope used for scanning the object are identified. Any sub-set or all of the options discussed herein are identified. The identification is through user input, sensing, or loading from memory. For example, the user inputs a dose 72, isotope and collimator 74, and well counter 70 as shown in FIG. 5.

For identifying the options, any of the user interfaces used for calibration are provided for the object scan. For example, the user interfaces of FIGS. 5, 7, and 11 are used. Different arrangements or user interface displays may be used due to the difference between calibrating and use to scan the object of interest. The isotope may be identified by text entry and/or selection from a drop down list. The drop down list or searching based on the text entry uses the standardized list of isotopes and/or a database of user-defined isotopes not included in the standardized list. The search functionality discussed above is used to identify characteristics of the isotope used to scan the object. Where multiple energy windows are available for the isotope of the liquid radiotracer, the user may select the main, primary, or photopeak energy window and the scatter energy window.

In act 64, the processor or the SPECT scanner calculates a dose correction. To calculate the dose correction, the cross-calibration factor or factors used for the assay and residual doses are loaded from the cross-calibration table. The received identities of the options are used to look-up the cross-calibration factors from the table. For example, the primary and scatter energy windows, well counter, collimator, detector, isotope, and dose are used to find the cross-calibration factor for this combination of options.

In the example of FIG. 4, the MiQC activity searches the cross calibration table to find the right cross calibration factors, and uses these factors to modify the assay and residue doses, respectively. The search may not locate a cross-calibration factor for the specific combination of options used for the object. A priority of ranking of options (same well counter but different collimator), interpolation, selection of closest neighbor, fuzzy logic, and/or other criterion may be used to select a cross-calibration factor based on the combination of options.

The corrected doses are recorded in a file and can be used reconstruction to generate quantitative images. Alternatively, the corrected doses are used without recording in a file. In yet another alternative, a difference between the corrected assay dose and the corrected residual dose is found to provide an injected dose for the object.

For example, the proper cross-calibration factor from the cross calibration table is found and used to correct the dose. The corrected dose is output. As shown in FIG. 11, as the data is loaded, most of the fields are automatically filled. The well counters that the site has are displayed in the two drop down lists. After user has selected the right well counters used for assayed dose and residual dose measurement, respectively, the corresponding detector sensitivities and the cross calibration factors are populated from the tables. The actual dose correction is performed after the user has entered the dose and clicked a continue button.

To correct the assay and/or residual dose, act 40 of FIG. 1 is performed. For example, the dose correction is calculated as follows. Denote $\alpha_a$=the assayed dose measurement based on the well count reading, $\alpha_r$=the residual dose measurement based on the well count reading, $T_{a2i}$=the time lags (minutes) from assay measurement to injection, $T_{i2r}$=the time lags (minutes) from injection to residual measurement, $T_{1/12}$=the half-life of the isotope, $\varphi_a$=the cross calibration factor for assay well counter, and $\varphi_r$=the cross calibration factor for residual well counter. The injected dose is modified from $\alpha_a$ to $\beta_a$ by $\beta_a=(\alpha_a/\varphi_a)\exp\{-\ln(2)/T_{1/2}\}$, and the residual dose is modified from $\alpha_r$ to $\beta_r$ by $\beta_r=(\alpha_r/\varphi_r)\exp\{\ln(2)/T_{1/2}\}$. Then, the corrected injected dose $\beta$ is simply the difference: $\beta=\beta_a-\beta_r$. Without the correction, the injected dose would be $\alpha_a-\alpha_r$.

In act 42, the processor or SPECT scanner estimates activity concentration in a patient having the isotope at the corrected dose measured by the well counter. The activity concentration is estimated from a scan by the SPECT system using the detector, collimator, and/or other options in a combination that is used to look-up the cross-calibration factor. The estimation is performed by reconstruction. The reconstruction incorporates a model of the SPECT scanner. The combination of options is used to look-up the system-specific planar sensitivity, which is included in the model for reconstruction. The activity concentration is estimated using the dose corrected with the dose correction factor or factors and using the system-specific sensitivity for the combination used to scan the object.

In act 44, an image of the activity concentration is generated as discussed above for FIG. 1. The activity concentration is used for imaging, or uptake values are calculated from the activity concentration and used for imaging. A quantitative SPECT image is generated based on the system-specific sensitivity and the cross-calibration factors looked-up from the tables.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for application of cross-calibration for a quantitative single photon emission computed tomography (SPECT) system, the method comprising:
   providing the SPECT system at a facility with the SPECT system having a detector configured to operate with different collimators to detect emissions from liquid radiotracers with injected dosages measured by well counters, the liquid radiotracers comprising isotopes;
   generating a first table of system specific planar sensitivities, the first table including one of the system specific planar sensitivities for each unique combination of isotope, energy of isotope, collimator, detector, and well counter;
   generating a second table of cross-calibration factors, the second table including one of the cross-calibration factors for each unique combination of the isotope, the collimator, the energy of the isotope, the detector, and the well counter, the cross-calibration factors being a function of the system specific planar sensitivities;
   receiving identities of a first one of the well counters used for a patient, a first one of the collimators used for the patient, a first one of the detector used for the patient, a first one of the doses used for the patient, and a first one of the isotopes used for the patient;
   calculating a dose correction with a first one of the cross-calibration factors selected based on the identities;
   estimating an activity concentration in a patient having the first isotope at the first dose measured by the first well counter, the activity concentration estimated in a scan by the SPECT system using the detector and first collimator, and estimated as a function of the calculated dose correction; and
   generating an image of the activity concentration.

2. The method of claim 1 wherein providing the SPECT system comprises providing the SPECT system with the different collimators, isotopes and well counters available at the facility.

3. The method of claim 1 wherein generating the first table comprises generating the first table with the system specific planar sensitivities from class planar sensitivities to the isotopes and a factory calibration source.

4. The method of claim 1 wherein for at least the first isotope, a plurality of main energy windows, scatter energy windows, or both occur, and wherein generating the first table comprises generating with the energies of the isotope selected from the main energy windows, scatter energy windows, or both.

5. The method of claim 1 wherein generating the first and second tables comprises identifying the isotopes from a standardized list and from a database of user-defined ones of the isotopes not included in the standardized list.

6. The method of claim 1 wherein calculating the dose correction comprises calculating from a difference between an assay dose and a residual dose, the assay dose corrected as a function of the first cross-calibration factors and the residual dose corrected as a function of a second cross-calibration factor.

7. The method of claim 1 wherein calculating the dose correction comprises calculating by look-up in the second table.

8. The method of claim 1 wherein generating the second table comprises generating the second table with look-up from the first table.

9. The method of claim 1 wherein estimating the activity concentration comprises estimating the activity concentration from the first dose as corrected by the dose correction and a first one of the system specific planar sensitivities.

10. The method of claim 1 wherein the generating of the first and second tables is performed using a first module during calibration, and the calculating and estimating are performed using a second module during a SPECT scan, the first and second module integrated in the SPECT system.

11. The method of claim 2 wherein generating the first and second tables comprises generating during a periodic calibration for the SPECT system at the facility.

12. The method of claim 4 wherein receiving identities comprises receiving user input of a first one of the main energy windows and a first one of the scatter energy windows, and wherein calculating the dose correction comprises calculating with the first cross-calibration factor selected based on the first main energy window and the first scatter energy window.

13. The method of claim 5 wherein receiving identities comprises receiving the identity of the first isotope, and further comprising searching the standardized list and the database of user-defined isotopes.

14. A non-transitory computer readable storage medium having stored therein data representing instructions executable by a programmed processor for application of cross-calibration in a single photon emission computed tomography (SPECT) system, the storage medium comprising instructions for:
- receiving input of identity of first and second radioactive sources;
- searching for characteristics of the first and second radioactive sources from a standardized list of sources and from a custom list of un-standardized sources;
- determining system-specific sensitivity for the SPECT system and a cross-calibration factor of radioactive sources, the determining based on the characteristics; and
- generating a quantitative SPECT image as a function of the system-specific sensitivity and the cross-calibration factor.

15. The non-transitory computer readable storage medium of claim 14 further comprising receiving input of identity of at least one well counter used to determine dose for the first radioactive source, and wherein determining the system-specific sensitivity and the cross-calibration factor comprises determining based on the at least one well counter.

16. The non-transitory computer readable storage medium of claim 14 wherein the characteristics comprises a plurality of energy windows for at least the first radioactive source;
- further comprising receiving user selection of a first of the energy windows as a photo-peak energy window and of a second of the energy windows as a scatter window; and
- wherein determining comprises determining the system-specific sensitivity and the cross-calibration factor based on the first and second energy windows.

17. A system for application of cross-calibration in functional imaging quantification, the system comprising:
- a functional imaging system with a detector;
- a well counter;
- a first isotope source;
- a second isotope source;
- a processor configured to determine a sensitivity for the detector, the sensitivity responsive to a measure by the well counter, and to determine a cross-calibration between the first and second isotope sources as a function of the sensitivity, the cross-calibration being specific to the well counter, wherein the processor is further configured to search a table of cross-calibrations including the cross-calibration based on a selection of the well counter and to correct a patient dose measured by the well counter, the correction being a function of the cross-calibration; and
- a memory configured to store the sensitivity and the cross-calibration in tables linked to the well counter.

18. The system of claim 17 wherein the functional imaging system comprises a single photon emission computed tomography system, wherein the detector comprises a planar gamma camera, and wherein the processor comprises a processor of the functional imaging system.

19. The system of claim 17 wherein the first isotope source has a plurality of energy windows, further comprising a user interface configured for selection of a first of the energy windows for a photo-peak window and selection of a second of the energy windows for a scatter window, and wherein the sensitivity and cross-calibration are determined specific to the photo-peak and scatter windows.

20. A system for application of cross-calibration in functional imaging quantification, the system comprising:
- a functional imaging system with a detector;
- a well counter;
- a first isotope source, wherein the first isotope source has a plurality of energy windows;
- a second isotope source;
- a processor configured to determine a sensitivity for the detector, the sensitivity responsive to a measure by the well counter, and to determine a cross-calibration between the first and second isotope sources as a function of the sensitivity, the cross-calibration being specific to the well counter;
- a memory configured to store the sensitivity and the cross-calibration in tables linked to the well counter; and
- a user interface configured for selection of a first of the energy windows for a photo-peak window and selection of a second of the energy windows for a scatter window, and wherein the sensitivity and cross-calibration are determined specific to the photo-peak and scatter windows.

* * * * *